United States Patent

Chauvette

[11] 3,932,393
[45] Jan. 13, 1976

[54] 3-METHYLENECEPHALOSPORINS AND PROCESS FOR PRODUCTION THEREOF

[75] Inventor: Robert R. Chauvette, Indianapolis, Ind.

[73] Assignee: Eli Lilly and Company, Indianapolis, Ind.

[22] Filed: Feb. 25, 1971

[21] Appl. No.: 118,941

[52] U.S. Cl.............................. 260/243 C; 424/246
[51] Int. Cl.² ........................................ C07D 501/18
[58] Field of Search ................................ 260/243 C

[56] References Cited
UNITED STATES PATENTS

| | | | |
|---|---|---|---|
| 3,647,788 | 3/1972 | Clark et al. ...................... | 260/243 C |
| 3,660,395 | 5/1972 | Wright et al. .................... | 260/243 C |
| 3,660,396 | 5/1972 | Wright ............................. | 260/243 C |

Primary Examiner—Nicholas S. Rizzo
Attorney, Agent, or Firm—William B. Scanlon; Everet F. Smith

[57] ABSTRACT

3-Methylenecepham-4-carboxylic acids and esters of the Formula I and 3-methyl-Δ³-cephem-4-carboxylic acids and esters of the Formula II

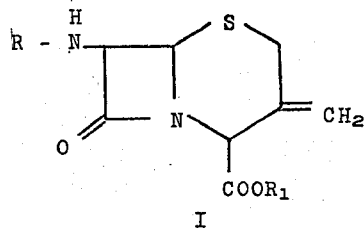

I

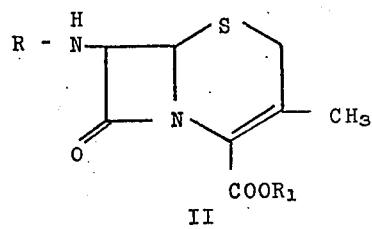

II where R is hydrogen or an organic acyl group and $R_1$ is hydrogen, $C_1$–$C_4$ alkyl a carboxylic acid protecting group or a pharmaceutically acceptable cation are prepared via the reductive displacement of a 3-substituted methyl cephalosporin of the Formula III

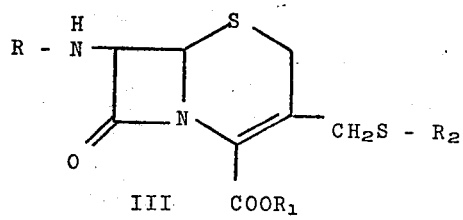

III where $R_2$ is an organic residue such that —$SR_2$ constitutes a reductively displaceable moiety, and R and $R_1$ have the same meanings as defined in Formulae I and II, reductive displacement being accomplished by catalytic hydrogenation or chemical reduction. The 3-methylene cepham compounds are isomerized in dimethylacetamide in the presence of a tertiary alkyl amine to provide 3-methyl-7-acylamido-Δ³-cephem-4-carboxylic acids and esters.

19 Claims, No Drawings

3-METHYLENECEPHALOSPORINS AND PROCESS FOR PRODUCTION THEREOF

BACKGROUND OF THE INVENTION

The cephalosporin antibiotics stem from the discovery of cephalosporin C produced in the fermentation of *Cephalosporium acremonium*.

The parent group of antibiotics possess in common the basic structural features represented by the following general formula for a 7-acylamidocephalosporanic acid

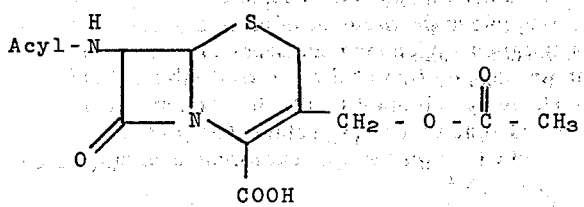

and are characterized by a β-lactam ring fused to a dihydrothiazine ring bearing an acetoxymethyl group in the 3-position; a carbon to carbon double bond in the 3-position and a carboxylic acid function in the 4-position. Cephalosporin C is represented by the above formula when the acyl group is 5-aminoadipoyl.

Numerous modifications have been made in the parent structure, including those in which the acetoxy function at the 3-methyl position has been replaced by another group.

Among the variations which have led to new and useful antibiotics have been the desacetoxycephalosporanic acids represented by the formula

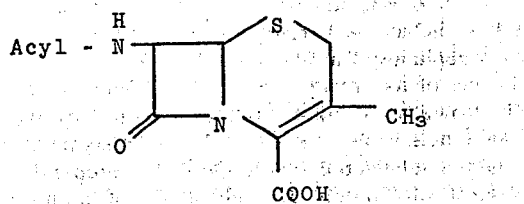

wherein the 3-position is substituted by a methyl group in place of the acetoxymethyl group of the cephalosporanic acids.

Heretofore, two general methods have been employed to prepare the desacetoxycephalosporanic acids. In the first of these methods, cephalosporin C is converted to 7-aminocephalosporanic acid (7-ACA) by cleaving the 5-aminoadipoyl side chain therefrom, for example, by the procedure described by Morin et al. in U.S. Pat. No. 3,188,311. The 7-ACA is then subjected to hydrogenolysis according to the method described in *J. Med. Chem.*, 7, 117 (1964) to provide 7-aminodesacetoxycephalosporanic acid (7-ADCA). Acylation of 7-ADCA with the desired acyl moiety according to well known acylation methods thus provides the 7-acylamidodesacetoxycephalosporanic acid.

The catalytic hydrogenolysis of cephalosporin C has been reported to yield desacetoxycephalosporin C, *Biochem J.*, 79, 377 (1961).

Alternatively, the desired desacetoxycephalosporanic acid can be prepared by the rearrangement of an appropriately substituted penicillanate sulfoxide ester according to the procedure described by U.S. Pat. No. 3,275,626, issued Sept. 27, 1966.

Although the preceding methods for the preparation of the desacetoxycephalosporanic acids are valuable synthetic methods, the search for more efficient and economical processes for the preparation of these antibiotics continues.

DESCRIPTION OF THE PRIOR ART

As discussed above, 7-aminodesacetoxycephalosporanic acid is a useful intermediate for the preparation of the desacetoxycephalosporanic acid antibiotics. For example, acylation of 7-ADCA in a mixed anhydride reaction with tert-butyloxycarbonyl (t-BOC) protected D-phenylglycine using methyl chloroformate followed by the removal of the t-BOC group provides 7-(α-D-aminophenylacetamido)desacetoxycephalosporanic acid, commonly known as cephalexin.

According to the cephem nomenclature system of the cephalosporin antibiotics, Morin, et al. *J. Am. Chem. Soc.*, 84, 3400 (1962), 7-ADCA is designated as 3-methyl-7-amino-$\Delta^3$-cephem-4-carboxylic acid, wherein the $\Delta^3$ refers to the endocyclic position of the carbon to carbon double bond. Other useful cephalosporin intermediates are known wherein the carbon to carbon double bond is located in the 2-position ($\Delta^2$) of the cephem ring, for example, the 7-acyl-$\Delta^2$-cephem-4-carboxylic acid esters described by U.S. Pat. No. 3,536,705 and *J. Org. Chem.*, 35, 2429 (1970). However, compounds of the cephem structure having an exocyclic double bond as shown in the formula below, have not been previously characterized in the prior art.

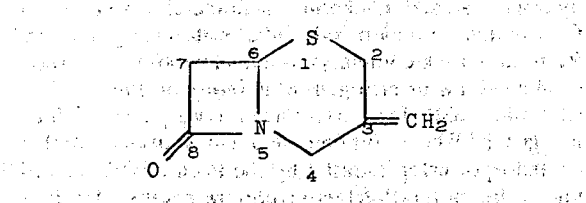

In U.S. Pat. No. 3,275,626 the proposed mechanism of the rearrangement of penicillin ester sulfoxides to desacetoxycephalosporanate esters is discussed. One of the proposed by-products of the rearrangement, depicted structurally in the discussion of the mechanism is an ester of a 7-acylamido-3-methylenecepham-4-carboxylic acid. This postulated product has not heretofore been described either in terms of its physical and chemical properties or in terms of its usefulness and no practical method for its preparation has as yet been described.

SUMMARY OF THE INVENTION

This invention relates to cephalosporin compounds having the 3-methylenecepham structural moiety. In particular this invention relates to 3-methylene-7- amino and 7-acylamidocepham-4-carboxylic acids, the salts and esters thereof and to a method for their production.

This invention further relates to a method for the preparation of desacetoxycephalosporanic acids and the salts and esters thereof.

The 3-methylenecepham compounds provided by the present invention are represented by the following structural Formula I

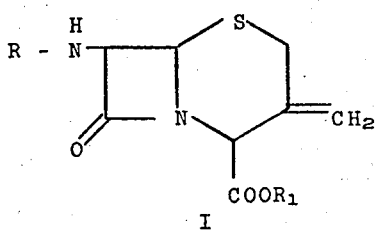

wherein R represents hydrogen or an organic acyl group and $R_1$ is hydrogen, an alkali, alkaline earth metal, or zinc cation, $C_1$–$C_4$ alkyl, or a carboxylic acid protecting ester moiety.

The 3-methylenecepham-4-carboxylic acids are prepared by the reduction of a 3-substituted methyl-$\Delta^3$-cephem-4-carboxylic acid represented by the Formula III

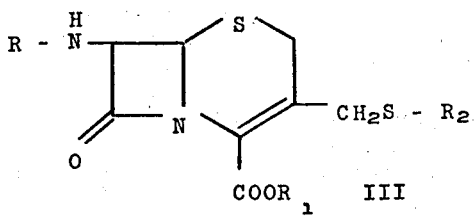

wherein R is hydrogen or an organic acyl group, $R_1$ is hydrogen, an alkali, alkaline earth metal or zinc cation, $C_1$–$C_4$ alkyl, or a carboxylic acid protecting group, and $R_2$ is an organic moiety which can contain carbon, oxygen, sulfur or nitrogen or an inorganic sulfo radical such that —$SR_2$ forms a reductively displaceable leaving group. The reduction of a 3-substituted methyl-cephalosporin represented by the Formula III, according to the method of this invention, results in the displacement of the group —$SR_2$, to yield predominantly a 3-methylenecephalosporin represented by the Formula I which is generally accompanied by the production of a 3-methylcephalosporin represented by the Formula II.

This novel reaction is designated as a reductive displacement reaction in that it proceeds under either catalytic hydrogenation conditions or under chemical reduction conditions with loss of the group $SR_2$ and formation of a 7-amino or 7-acylamidocepham-4-carboxylic acid having an exocyclic double bond in the 3-position and varying amounts of the correspondingly 7-substituted 3-methyl-$\Delta^3$-cephem.

The reductive displacement reaction is carried out by dissolving the 3-substituted methyl-7-amino or 7-acylamido-$\Delta^3$-cephem-4-carboxylic acid, a salt or an ester thereof in a suitable solvent and reacting the solution with hydrogen maintained at a pressure between about 15 and 500 psi. in the presence of a hydrogenation catalyst. The reaction is performed at a temperature between about 15° and 60°C. and preferably at about 25° to 45°C. The preferred hydrogenation catalyst is Raney nickel.

The reductive displacement reaction is also effected under chemical reduction conditions in the presence of dimethylformamide (DMF) by employing as the reducing agent a metal-acid combination, such as zinc in the presence of a carboxylic acid having a pKa value below about pKa 4.0, for example, formic acid or a dilute mineral acid; a bimetallic couple such as the zinc-copper couple in the presence of an acid; an amalgamated metal such as aluminum amalgam and zinc amalgam in the presence of an acid or an oxidizable metallic salt such as the chromous salts, for example, chromous chloride and chromous acetate. The preferred chemical reducing agent is zinc and formic acid in the presence of DMF.

The 3-methylene-7-amino or 7-acylamidocepham-4-carboxylic acids and esters are valuable chemical intermediates useful for the synthesis of the 3-methyl-$\Delta^3$-cephem antibiotics, the desacetoxycephalosporanic acids. Thus in another of its aspects the present invention provides a novel method for the isomerization of a 3-methylenecepham compound to a 3-methyl-$\Delta^3$-cephem antibiotic compound. The isomerization is carried out by dissolving the desired 3-methylene-7-amino or 7-acylamidocepham acid or ester in an isomerization medium comprising an aprotic solvent with a high dielectric constant such as dimethylacetamide and a tertiary amine base having a pK'a of at least 9.5 and preferably triethylamine.

The starting materials employed in the preparation of the 3-methylenecepham acid salts and esters, the 3-substituted methyl-$\Delta^3$-cephem acids, have been previously described and are prepared according to known methods. In general, the starting materials are obtained by reacting a 7-amino or a 7-acylamidocephalosporanic acid (a 3-acetoxymethyl-$\Delta^3$-cephem acid) for example, phenoxyacetamidocephalosporanic acid with a sulfur nucleophile $HSR_2$, for example, thiobenzoic acid or thiourea, to effect the nucleophilic displacement of the acetoxyl group and provide a 3-substituted methylcephalosporin of the Formula III.

In one of its broader aspects the present invention thus provides a method for preparing a 3-methyl-$\Delta^3$-cephem acid, salt or ester from a 3-acetoxymethyl-$\Delta^3$-cephem acid which comprises, first, the preparation of a 3-substituted methyl-$\Delta^3$-cephem acid of the prior art via the nucleophilic displacement reaction with a compound $HSR_2$, and secondly the reductive displacement reaction of this invention whereby the group $SR_2$ is displaced to provide a 3-methylenecepham acid, salt or ester, and finally the isomerization of the exo double bond of the 3-methylenecepham acid or ester to afford the 3-methyl-$\Delta^3$-cephem acid or ester.

The foregoing reaction sequence is illustrated by the following general reaction scheme.

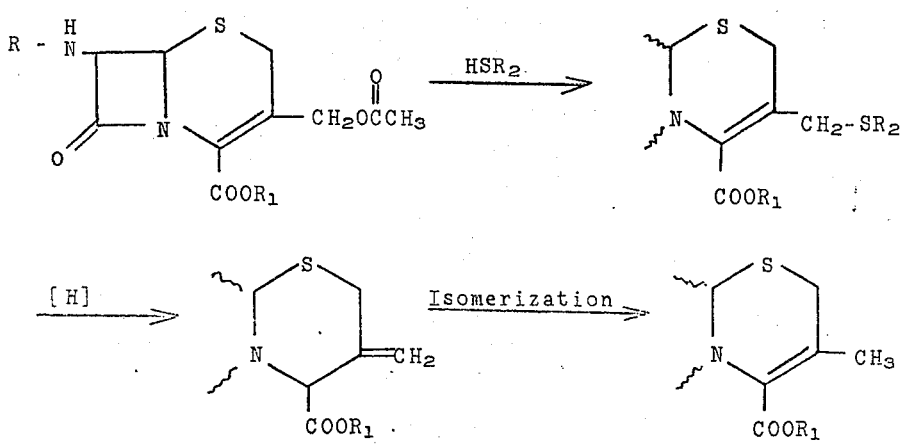

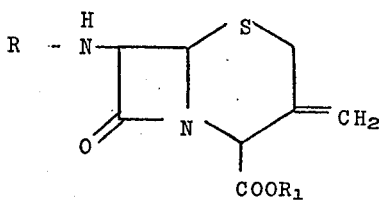

DETAILED DESCRIPTION

The 3-methylenecephalosporin compounds provided by the present invention are represented by the following structural Formula I:

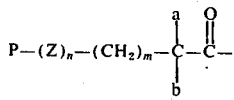

wherein:
R₁ is hydrogen, $C_1-C_4$ alkyl a carboxylic acid protecting group or a pharmaceutically acceptable cation,
R is hydrogen, $C_1-C_8$ alkanoyl, $C_6-C_{10}$ cycloalkanoyl, $C_2-C_8$ hydroxyalkanoyl, $C_3-C_8$ alkanoyl substituted by carboxy and amino or protected amino, benzoyl, substituted benzoyl, or an acyl group represented by the formula $$P-(Z)_n-(CH_2)_m-\underset{b}{\overset{a}{C}}-\overset{O}{\underset{}{C}}-$$

wherein P is α-thienyl, β-thienyl, α-furyl, β-furyl, benzothienyl, benzofuryl, phenyl or substituted phenyl,
Z is oxygen or sulfur,
n is 0 or 1,
m is an integer of from 0 to 3
a is hydrogen, $C_1-C_3$ lower alkyl,
b is hydrogen, $C_1-C_3$ lower alkyl, hydroxy, amino or protected amino,
and when n is 1, P is phenyl or substituted phenyl and b is other than hydroxy, amino or protected amino.

The term, "$C_1-C_8$ alkanoyl" as used herein refers to formyl, acetyl, propionyl, n-butyryl, isobutyryl, valeryl, caproyl, heptanoyl, isoocantoyl and the like. "$C_6-C_{10}$ cycloalkanoyl" refers to cyclopentanoyl, cyclohexanoyl, 4-methylcyclohexanoyl, cycloheptanoyl, 3-methylcycloheptanoyl, 3-ethylcyclohexanoyl, 3,4-dimethylcyclopentanoyl and the like. "$C_2-C_8$ hydroxyalkanoyl" refers to glycoloyl, α-hydroxypropionyl, β-hydroxybutyryl, γ-hydroxybutyryl, γ-hydroxyvaleryl and like hydroxy substituted alkanoyl radicals. The term "$C_3-C_8$ alkanoyl substituted by carboxy and amino" refers to the amino acid radicals such as 5'-aminoadipoyl, 2'-aminosuccinoyl, 4'-aminoglutaroyl, 7'-aminosuberoyl and the like. Substituted benzoyl refers to benzoyl substituted on one or more carbon atoms of the benzene ring thereof with $C_1-C_3$ alkyl, $C_1-C_3$ alkoxy, halogen or amino, for example, 4-methylbenzoyl, 4-isopropylbenzoyl, 3,4-dimethylbenzoyl, 4-chlorobenzoyl, 3-bromobenzoyl, 4-methoxybenzoyl, 3-methoxy-4-ethoxybenzoyl, 3-isopropoxybenzoyl, 2-aminobenzoyl, 3-amino-4-methylbenzoyl and like substituted benzoyl groups.

The term "substituted phenyl" refers to phenyl substituted at one or more ring positions by $C_1-C_3$ alkyl, $C_1-C_3$ alkoxy, hydroxy, halogen or amino, for example, 3,4-dimethylphenyl, 4-ethylphenyl, 4-isopropylphenyl, 4-methoxyphenyl, 4-methoxy-3-ethoxyphenyl, 4-isopropoxyphenyl, 3,4-dichlorophenyl, 3-hydroxyphenyl, 2-bromophenyl, 4-fluorophenyl, 3,4-dihydroxyphenyl, 2-hydroxyphenyl, 4-aminophenyl, 4-acetamidophenyl and the like.

"Carboxylic acid protecting group" refers to the organic ester or anhydride forming radicals which are commonly employed in the protection of the carboxylic acid function of the penicillin and cephalosporin antibiotics and more generally for the protection of the carboxylic acid function of amino acids and peptides. Such protecting groups are those which are relatively labile and susceptible to cleavage under acid or base hydrolytic or hydrogenolytic conditions and includes, for example, the tert-butyl, benzyl, p-methoxybenzyl, 2,2,2-trichloroethyl, p-nitrobenzyl, benzyhydryl, 4methoxybenzylhydryl, phenacyl, p-bromophenacyl, tetrahydropyranyl esters and the mixed anhydrides formed with acetic and propionic acids.

"Pharmaceutically acceptable cation" refers to the alkali metal cations such as the lithium, sodium and potassium cations and the alkaline earth metal cations such as the calcium and magnesium cations and the zinc cation.

The terms "halo" and "halogen" as used in this description refer to fluoro, chloro, bromo and iodo.

The term "protected amino" as used herein refers to a primary amino group substituted by one of the commonly employed amine blocking groups such as tert-butyloxycarbonyl, benzyloxycarbonyl, substituted benzyloxycarbonyl, trichloroethyloxycarbonyl, adamantyloxycarbonyl, trifluoroacetyl, chloroacetyl, pentane-1,3-dione, phthaloyl, formyl and like amine blocking groups which are commonly employed in the antibiotic and polypeptide arts.

The novel compounds represented by the Formula I where R is H or an organic acyl group containing a free amino group, for example 5'-aminoadipoyl, and where R₁ is hydrogen are capable of existing in the zwitterionic form. For example where R and R₁ are both hydrogen, the compound represented is 3-methylene-7-aminocepham-4-carboxylic acid, or where R is α-phenylglycyl and R₁ is H, the compound represented is 7-(D-α-phenylglycylamido)-3-methylenecepham-4-carboxylic acid. Both such compounds can exist in the zwitterionic forms, which forms are to be understood as included within the scope of the present invention.

Illustrative of the acyl groups represented by R in Formula I are formyl, acetyl, propionyl, hexanoyl, phenylacetyl, phenoxyacetyl, 4-methylphenylacetyl, 4-chlorophenylacetyl, α-thienylacetyl, β-thienylacetyl, β-phenylpropionyl, α-furylacetyl, β-furylacetyl, benzoyl, phenylmercaptoacetyl, α-benzofurylacetyl, α-benzothienylacetyl, valeryl, 3,4-dimethylphenylacetyl, 4-methoxyphenylacetyl, o-tolylmercaptoacetyl, 5'-aminoadipoyl, α-amino-α-phenylacetyl, 5'-(chloroacetamido)adipoyl, 5'-(formamido) adipoyl, 5'-(phthalimido)adipoyl, α-hydroxy-α-phenylacetyl, α-amino-α-(3-hydroxyphenyl) acetyl, cyclopentylacetyl, 3-chlorophenylmercaptoacetyl, 2-bromophenylmercaptoacetyl, α-phenoxyisoamoyl, α-phenoxyisobutanoyl, α-phenoxy-n-butanoyl, α-(4-methoxyphenoxy) isobutanoyl radicals.

Specific examples of the compounds included within the scope of the present invention are the following:
3-methylene-7-aminocepham-4-carboxylic acid
benzyl 3-methylene-7-aminocepham-4-carboxylate
3-methylene-7-acetamidocepham-4-carboxylic acid
3-methylene-7-phenylacetamidocepham-4-carboxylic acid
3-methylene-7-phenoxyacetamidocepham-4-carboxylic acid
3-methylene-7-[2'-(α-thienyl)acetamido]cepham-4-carboxylic acid
3-methylene-7-[2'-(α-thienyl)acetamido]cepham-4-carboxylic acid
tert-butyl 3-methylene-7-[2'-(3-hydroxyphenyl)-2'-aminoacetamido]-cepham-4-carboxylate
3-methylene-7-[2'-(3-hydroxyphenyl)-2'-aminoacetamido]cepham-4-carboxylic acid
3-methylene-7-[2'-(α furyl)acetamido]cepham-4-carboxylic acid
3-methylene-7-[2'-(β-thienyl)-2'-aminoacetamido]-cepham-4-carboxylic acid
3-methylene-7-(2'-phenyl-2'-aminoacetamido)cepham-4-carboxylic acid
3-methylene-7-n-valeramidocepham-4-carboxylic acid
3-methylene-7-caprylamidocepham-4-carboxylic acid
3-methylene-7-[2'-(α-benzothienyl)acetamido]-cepham 4-carboxylic acid
2,2,2-trichloroethyl 3-methylene-7-(2'-phenoxyacetamido)cepham-4-carboxylate
3-methylene-7-(2'-phenoxy-2',2'-dimethylacetamido)-cepham-4-carboxylic acid
3-methylene-7-(2'-phenyl-2'-hydroxyacetamido)cepham-4-carboxylic acid
3-methylene-7-[2'-(4-methylphenyl)acetamido]cepham-4-carboxylic acid
3-methylene-7-(5'-aminoadipamido)cepham-4-carboxylic acid
p-nitrobenzyl 3-methylene-7-(2'-phenoxyacetamido)-cepham-4-carboxylate
3-methylene-7-propionamidocepham-4-carboyxlic acid
3-methylene-7-isovaleramidocepham-4-carboxylic acid
3-methylene-7-n-butyramidocepham-4-carboxylic acid
3-methylene-7-benzoylcepham-4-carboxylic acid
3-methylene-7-cyclopentamidocepham-4-carboxylic acid
benzhydryl 3-methylene-7 -cyclohexanamidocepham-4-carboxylate
p-nitrobenzyl 3-methylene-7-aminocepham-4-carboxylate
p-methoxybenzyl 3-methylene-7-aminocepham-4-carboxylate
3-methylene-7-[2'-(4-methoxyphenyl)acetamido]-cepham-4-carboxylic acid
3-methylene-7-[2'-(4-chlorophenyl)acetamido]cepham-4-carboxylic acid
3-methylene-7-(2'-phenoxy-2'-ethylacetamido)cepham-4-carboxylic acid
3-methylene-7-[2'-(3-aminophenyl)acetamido]cepham-4-carboxylic acid
2,2,2-trichloroethyl 3-methylene-7-aminocepham-4-carboxylate
3-methylene-7-(5'-hydroxyvaleramido)cepham-4-carboxylic acid
3-methylene-7-[2'-(α-benzofuryl)acetamido]cepham-4-carboxylic acid
t-butyl 3-methylene-7-aminocepham-4-carboxylate
phenacyl 3-methylene-7-aminocepham-4-carboxylate
3-methylene-7-formamidocepham-4-carboxylic acid
3-methylene-7-(5'-acetylaminoadipamido)cepham-4-carboxylic acid
3-methylene-7-(5'-phthaloylaminoadipamido)cepham-4-carboxylic acid
benzyl 3-methylene-7-[2'-(α-thienyl)acetamido]cepham-4-carboxylate
3-methylene-7-[2'-(o-tolylmercapto)acetamido]cepham-4-carboxylic acid
3-methylene-7-[2'-(m-chlorophenylmercapto)acetamido]cepham-4-carboxylic acid
3-methylene-7-(phenylmercaptoacetamido)cepham-4-carboxylic acid
t-butyl 3-methylene-7-[2'-(o-methoxyphenylmercapto)acetamido]-cepham-4-carboxylate
3-methylene-7-[2'-(p-ethoxyphenylmercapto)acetamido]cepham-4-carboxylic acid
3-methylene-7-(5'-propionylaminoadipamido)cepham-4-carboxylic acid
3-methylene-7-(5'-propionylaminoadipamido)cepham-4-carboxylic acid di-p-nitrobenzyl ester.
p-nitrobenzyl 3-methylene-7-(α-aminophenylacetamido)cepham-4-carboxylate
3-methylene-7-(5'-thiobenzoylacetylaminoadipamido)cepham-4-carboxylic acid The 3-methylenecepham-4-carboxylic acids provided by this invention are in general highly crystalline compounds exhibiting, in many cases, enhanced water solubility in comparison with the correspondingly substituted 3-methyl-Δ³-cephem-4-carboxylic acids (desacetoxycephalosporanic acids). In contrast to the 3-methyl-α³-cephem-4-carboxylic acids, the 3-methylenecepham compounds do not display absorption in the 260 mμ region of the ultraviolet spectrum but, like the 3-methyl-Δ³-cephem compounds, they show absorption at about 1790 cm.⁻¹ in the infrared region of the spectrum characteristic of the β-lactam carbonyl. The nuclear magnetic resonance spectra of the 3-methylenecepham compounds show the presence of an allylic type hydrogen at $C_4$ and two vinylic hydrogens attached to a carbon substituent at $C_3$, characteristics which are in agreement with the structure of the 3-methylenecepham-4-carboxylic acids designated herein.

The novel 3-methylenecephalosporin compounds are prepared by reacting under reducing conditions a 7-amino or a 7-acylamido-$\Delta^3$-cephem-4-carboxylic acid or ester substituted in the 3-position of the cephem nucleus by a group represented by the formula — $CH_2$ — S — $R_2$ wherein $R_2$ represents an organic radical, or the $SO_3^-$ $M^+$ group wherein $M^+$ is a metallic cation.

According to the practice of this invention, the 3-methylenecephalosporins of Formula I are prepared with a 3-substitutedmethylcephalosporin represented by the Formula III.

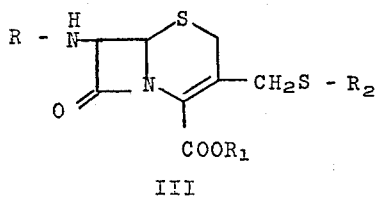

III wherein
R has the same meanings as previously assigned in Formula I,
$R_1$ is hydrogen, an alkali, alkaline earth metal or zinc cation, or a carboxylic acid protecting group,
$R_2$ is $C_2$-$C_4$ alkanoyl, $C_2$-$C_4$ haloalkanoyl, benzoyl, substituted benzoyl, $C_1$-$c_4$ lower alkyl, $C_1$-$C_{12}$ alkoxythionocarbonyl, an amidino or substituted amidino group of the formula

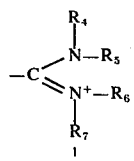

wherein $R_4$, $R_5$, $R_6$ and $R_7$ are the same or different and each represents hydrogen, $C_1$-$C_6$ alkyl, $C_3$-$C_7$ cycloalkyl, aryl, aralkyl, substituted aryl or substituted aralkyl, a thiocarbamoyl group of the formula

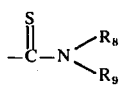

wherein $R_8$ and $R_9$ when taken separately are the same or different and are hydrogen, $C_1$-$C_6$ alkyl, phenyl or substituted phenyl and $R_8$ $R_9$ when taken together form a 4 or 5 membered alkylene, azaalkylene or oxaalkylene bridge,
a monocyclic heteroaryl or bicyclic heteroaryl group containing nitrogen, sulfur or oxygen,
or a sulfo group of the formula — $SO_3^-$ $M^+$
wherein $M^+$ is an alkali or alkaline earth metal cation, and when $R_2$ is an amidino or a substituted amidino group, $R_1$ is hydrogen, or when $R_2$ is — $SO_3^-$ $M^+$, $R_1$ is also $M^+$.

Illustrative of the readily displaceable nucleophilic groups represented by - S - $R_2$ are

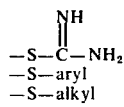

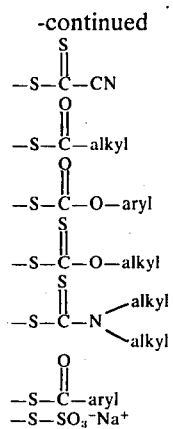

and the like. The term "Aryl" refers to phenyl, $\alpha$-naphthyl of $\beta$-naphthyl and "aralkyl" refers to benzyl, $\beta$-phenethyl, 3-phenylpropyl, $\alpha$-naphthylmethyl, 2-($\beta$-naphthyl)ethyl and the like and "substituted phenyl" and "substituted aralkyl" refers to such aryl and aralkyl groups substituted on one or more ring positions by $C_1$-$C_4$ lower alkyl, $C_1$-$C_4$ lower alkoxy, halogen, amino or hydroxy.

When in the above Formula III, $R_2$ represents a thiocarbamoyl group of the formula

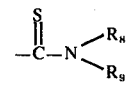

and $R_8$ and $R_9$ are taken together to form a 4- or 5-membered alkylene, azaalkylene or oxalkylene bridge with the nitrogen, the groups represented thereby are illustrated by pyrrolidinothiocarbonyl, piperidinothiocarbonyl, piperazinothiocarbonyl, morpholinothiocarbonyl and the like.

When $R_2$ represents "a monocyclic heteroaryl or a bicyclic heteroaryl" $R_2$ is representative of such groups as pyridyl, 2-pyrimidyl, 2-imidazolyl, 2-benzimidazolyl, 2-thiazolyl, 2-benzthiazolyl, 2-benzoxazolyl, 2-tetrazolyl, 1-methyl-2-tetrazolyl, thiadiazoyl, 2-methyl-5-thiadiazoyl and the like.

The compounds represented by the Formula III are prepared according to methods previously practiced in the cephalosporin antibiotic art. In general they are prepared by a nucleophilic displacement reaction of a cephalosporanic acid with a nucleophile represented by H - S - $R_2$. More particularly, the compounds represented by the Formula III, wherein $R_2$ is $C_1$-$C_{12}$ alkoxythionocarbonyl, are prepared according to the procedure described by U.S. Pat. No. 3,446,803. When $R_2$ represents an amidino or substituted amidino group, the 7-acylamidocephalosporin iso-thiouronium salts or substituted iso-thiouronium salts represented thereby are prepared and described according to U.S. Pat. No. 3,278,531. Likewise, the preparation and properties of the remaining compounds represented by the Formula III are described by U.S. Pat. Nos. 3,261,832, 3,239,516, and 3,243,435.

Examples of 3-substituted methylcephalosporins represented by the Formula III are the following:
3-amidinothiomethyl-7-(2'-phenoxyacetamido)-$\Delta^3$-cephem-4-carboxylic acid, inner salt,
3-amidinothiomethyl-7-(2'-phenylacetamido)-$\Delta^3$-cephem-4-carboxylic acid, inner salt, 3-methylthiomethyl-7-[2'-(α-thienyl)acetamido]-Δ³-cephem-4-carboxylic acid, 3-methylthiomethyl-7-acetamido-Δ³-cephem-4-carboxylic acid, 3-amidinothiomethyl-7-(D-2'-hydroxy-2'-phenylacetamido)-Δ³-cephem-4-carboxylic acid, inner salt, 3-benzoylthiomethyl-7-(D-2'-amino-2'-phenylacetamido)-Δ³-cephem carboxylic acid, benzyl 3-benzoylthiomethyl-7-caprylamido-Δ³-cephem-4-carboxylate, 3-amidinothiomethyl-7-[2'-(α-thienyl)-2'-aminoacetamido]-Δ³-cephem-4-carboxylic acid, inner salt, t-butyl 3-benzoylthiomethyl-7-(2'-phenoxyacetamido)-Δ³-cephem-4-carboxylate, 3-benzoylthiomethyl-7-amino-Δ³-cephem-4-carboxylic acid p-nitrobenzyl 3-ethoxythionocarbonylthiomethyl-7-(D-2'-amino-2'-phenylacetamido)-Δ³-cephem-4-carboxylate, 3-isopropoxythionocarbonylthiomethyl-7-[2'-(α-thienyl)acetamido]-Δ³-cephem-4-carboxylic acid, phenacyl 3-ethoxythionocarbonylthiomethyl-7-propionamido-Δ³-cephem-4-carboxylate, 3-(2-pyridylthiomethyl)-7-[2'-(α-thienyl)acetamido]-Δ³-cephem 4-carboxylic acid, 3-(2-benzimidazolylthiomethyl)-7-(2'-phenoxyacetamido)-Δ³-cephem-4-carboxylic acid, 3-(methylthionocarbonylthiomethyl)-7-[2'-(β-furyl)acetamido]-Δ³-cephem-4-carboxylic acid, 3-piperazinothionocarbonylthiomethyl-7-(2'-phenoxyacetamido)-Δ³-cephem-4-carboxylic acid, 3-benzoylthiomethyl-7-(5'-amino-5'-carboxyvaleramido))-Δ³-cephem 4-carboxylic acid, 3-benzoylthiomethyl-7-[5'-(2-benzoylthioacetamido)-5'-carboxyvaleramido-Δ³-cephem-4-carboxylic acid, 3-ethoxythionocarbonylthiomethyl-7-(5'-propionamido-5'-carboxy-valeramido)-Δ³-cephem-4-carboxylic acid, 3-p-nitrobenzoylthiomethyl-7-acetamido-Δ³-cephem-4-carboxylic acid, 3-[5-(1-methyl-2-tetrazolyl)thiomethyl]-7-[2'-(α-thienyl)-acetamido]-Δ³-cephem-4-carboxylic acid, 3-methylthionocarbonylthiomethyl-7-amino-Δ³-cephem-4-carboxylic acid, benzhydryl 7-[5'-benzoylthioacetamido)-5'-(carbodiphenylmethoxy)-valeramido]-3-benzoylthiomethyl-Δ³-cephem-4-carboxylate, 3-amidinothiomethyl-7-(5'-formamido-5'-carboxyvaleramido)-Δ³-cephem-4-carboxylic acid, inner salt, 3-ethoxythionocarbonylthiomethyl-7-(5'-amino-5'-carboxyvaleramido)-Δ³-cephem-4-carboxylic acid, 3-ethoxythionocarbonylthiomethyl-7-[2'-(α-thienyl)acetamido]-Δ³-cephem-4-carboxylic acid, 3-ethoxythionocarbonylthiomethyl-7-(2'-amino-2'-phenylacetamido)-Δ³-cephem-4-carboxylic acid, 3-sulfothiomethyl-7-[2'-(α-thienyl)acetamido]-Δ³-cephem-4-carboxylic acid disodium salt, 3-sulfothiomethyl-7-(5'-amino-5'-carboxyvaleramido)-Δ³-cephem-4-carboxylic acid, disodium salt, 3-benzoylthiomethyl-7-(5'-phthalimido-5'-carboxyvaleramido)-Δ³-cephem-4-carboxylic acid, 3-(4-nitrobenzoylthiomethyl)-7-formamido-Δ³-cephem-4-carboxylic acid, 3-sulfothiomethyl-7-phenylacetamido-Δ³-cephem-4-carboxylic acid, di-potassium salt, 3-sulfothiomethyl-7-acetamido-Δ³-cephem-4-carboxylic acid, di sodium salt, 3-sulfothiomethyl-7-amino-Δ³-cephem-4-carboxylic acid, di sodium salt, 3-ethoxythionocarbonylthiomethyl-7-[2'-(2-methoxycarbonyl-1-methylvinylamino)-2'-phenylacetamido]-Δ³-cephem-4-carboxylic acid.

According to the present invention a compound of the Formula III is reacted with hydrogen under reducing conditions comprising either catalytic hydrogenation conditions or chemical reduction conditions to provide a 3-methylenecephalosporin of the Formula I. The reductive displacement reaction is illustrated by the following general equation:

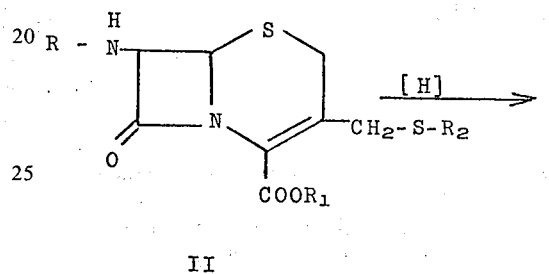

II

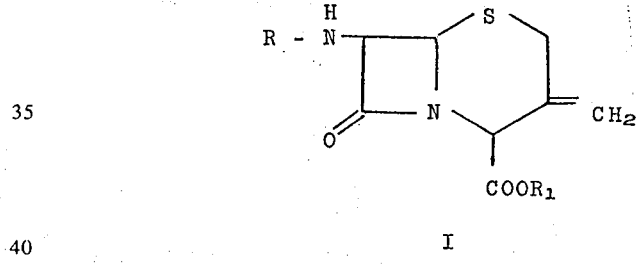

I wherein R, $R_1$ and $R_2$ have the same meanings as previously assigned. The reaction is characterized herein as a reductive displacement reaction in that, under the reducing conditions employed, the group S - $R_2$ is displaced with the formation of an exocyclic double bond in the 3-position of the cepham ring. The group $SR_2$ can be characterized as a leaving group, displaced under the reducing conditions employed.

The reductive displacement reaction is carried out with molecular hydrogen in the presence of a metallic hydrogenation catalyst or with nascent hydrogen formed by a reactive metallic couple, an amalgamated metal or the combination of a metal and acid in the presence of DMF. The reductive displacement reaction can also be carried out with the salts of chromium in the +2 valence state.

The reductive displacement reaction is carried out under catalytic hydrogenation conditions by dissolving a 3-substituted methyl cephalosporanic acid or an ester or cationic salt thereof in a suitable solvent and hydrogenating the solution in an atmosphere of hydrogen maintained at a pressure between about 15 and about 500 psi. The hydrogenation can be conducted at a temperature between about 5° and 65°C. and preferably at about 25° to 45°C. Hydrogenation catalysts which are effective in the reaction include the base metal catalysts such as nickel and cobalt, preferably the activated catalysts of the Raney type such as Raney nickel and Raney cobalt, and the noble metal catalysts such as platinum, palladium and rhodium. The preferred hydrogenation catalyst is Raney nickel.

The catalytic reduction can be carried out in a variety of solvents. In general, any aqueous or non-aqueous solvent which is unreactive with respect to the starting material, and preferably one that is not itself reduced, can be used. For example, methanol, ethanol, isopropanol, dimethylformamide, dioxane, tetrahydrofuran and the like, either alone or in admixture with water are suitable solvents. When the 3-substituted methyl cephalosporin is employed in a salt form, water alone can be used as the solvent.

The hydrogenation is allowed to proceed for about 24 hours at the preferred temperature range, although at somewhat higher temperatures the reaction proceeds more quickly.

The reductive displacement reaction can also be carried out under chemical reducing conditions well known in the art, whereby nascent hydrogen is generated or a readily oxidizable metallic salt functions as the reducing agent. Chemical reducing agents which can be employed in the present preparative method include metallic zinc in the presence of suitable acid, amalgamated metals such as zinc amalgam and aluminum amalgam, bimetallic couples such as the zinc-copper couple, and the salts of oxidizable metals, for example chromous chloride, chromous bromide, chromous acetate and the like.

The chemical reduction is carried out in an aqueous medium containing dimethylformamide (DMF) or dimethylacetamide (DMA) and if necessitated by the solubility of the particular 3-substituted methyl cephalosporin a co-solvent such as a water miscible ether solvent can be added. Co-solvents which can be employed include tetrahydrofuran, dioxane and the like.

The reduction is carried out with any of the above chemical reducing agents for about 6 to 24 hours at a temperature between about 0° and 60°C. The preferred temperature of reaction appears to be between about 15° and 45°C.

When an amalgamated metal is employed in the reductive displacement reaction, a solvent system comprising water, an alcoholic solvent such as ethanol and dimethylformamide is employed. When zinc or a metallic couple are employed a desirable solvent system comprises a mixture of water, a water miscible co-solvent such as tetrahydrofuran, dimethylformamide and an acid such as formic acid.

The preferred chemical reducing agent of the present method is zinc in the presence of an acid. Acids which can be employed in combination with zinc include dilute aqueous mineral acids such as hydrochloric acid and sulfuric acid of a concentration of about 0.5 to 5 percent or a carboxylic acid having a pKa of less than 4.0 such as formic acid, the chlorinated acetic acids such as the mono-, di- and trichloroacetic acids. A preferred acid is formic acid.

As previously mentioned, the chemical reduction is carried out in the presence of dimethylformamide or dimethylacetamide. The amount of DMF or DMA which is employed is not critical, provided it is present in a catalytic amount corresponding to at least about one percent by weight of the amount of reducing agent employed. It is preferable, however, to employ a larger amount of DMF or DMA to enhance the solubility of the starting material in certain instances.

The chemical reducing agent is preferably employed in excess. For example, the preferred reducing agent, zinc, is employed in an amount corresponding to from about 2 gram atoms to 10 gram atoms of zinc per gram of 3-substituted methyl cephalosporin employed.

Likewise, the acid used in combination with the reducing agent is preferably employed in excess.

In a preferred embodiment of the present method a 3-substituted methyl cephalosporin of the Formula III, for example, 300 mg. of 3-ethoxythionocarbonylthiomethyl-7-phenoxyacetamido-$\Delta^3$-cephem-4-carboxylic acid, (0.6 mmoles) is dissolved in a solvent mixture of 5.5 ml. of tetrahydrofuran, 1.5 ml. of water, 1.5 ml. of formic acid and 1.5 ml. of DMF and 700 mg. of zinc dust is added. The reaction mixture is stirred for 18 hours at ambient temperature to afford 3-methylene-7-phenoxyacetamidocepham-4-carboxylic acid as the predominant product.

The reductive displacement reaction can be carried out on a 3-substituted methyl cephalosporin as the free acid or as a salt or ester thereof. However, when the carboxylic acid protecting group is an acid labile ester or anhydride forming group and the preferred chemical reducing agent, zinc in the presence of formic acid, is employed the labile ester can undergo extensive cleavage to yield the 3-methylene cepham of the Formula I in the free acid form.

When $R_1$ is the Formula III represents a carboxylic acid protecting ester group such as benzyl, benzhydryl or P-methoxy-benzyl and the hydrogenation is carried out with Raney nickel the ester group remains substantially intact during the reductive displacement reaction. A like result is obtained when zinc in the presence of formic acid is employed. However, when palladium or supported palladium is used as the hydrogenation catalyst with a benzyl, substituted benzyl or benzhydryl ester, considerable hydrogenolysis of the ester group can occur, particularly when the reductive displacement reaction is carried out at higher temperatures.

Consequently, when it is desired to prepare a 3-methylenecepham-4-carboxylate of the Formula I, wherein $R_1$ is a carboxylic acid protecting group which is susceptible to cleavage under the conditions of the reductive displacement reaction, the unprotected 3-methylenecepham-4-carboxylic acid can be first prepared. Following the reductive displacement reaction the 3-methylenecepham-4-carboxylic acid reduction product can be isolated and then protected with the desired ester group by esterification or the mixed anhydride thereof with acetic or propionic acid can be prepared according to well known procedures. For example, 3-ethoxythionocarbonylthiomethyl-7-amino-$\Delta^3$-cephem-4-carboxylic acid, obtained by the reaction of 7-aminocephalosporanic acid (7ACA) with ethyl xanthate, is hydrogenated in the presence of Raney nickel to yield 3-methylene-7-aminocepham-4-carboxylic acid. The cepham acid is then acylated and esterified according to known procedures to obtain the desired ester of the Formula I.

When $R_2$ in the Formula III represents the group
$-SO_3^-M^+$
the compounds represented thereby undergo the reductive displacement reaction under catalytic hydrogenation conditions, preferably in the presence of Raney nickel catalyst, to yield the 3-methylene cepham of the Formula I in satisfactory yields. However, when the reductive displacement reaction is carried out under acidic chemical reducing conditions as, for example, with zinc in the presence of formic acid and DMF, only minor amounts of the 3-methylenecepham-4-carboxylic acid or ester is formed.

The production of the 3-methylene-7-acylamidocepham-4-carboxylic acids, esters and salts represented by the Formula I according to the above-described reductive displacement reaction is accompanied generally by the production of the corresponding isomer 3-methyl-7-acylamido-$\Delta^3$-cephem-4-carboxylic acids, esters or salts, and in some instances the corresponding 3-methyl-$\Delta^2$-cephem isomer has been observed.

The reduction product mixture comprising the 3-methylene-cepham and the 3-methyl-$\Delta^3$ and $\Delta^2$ cephem acids, esters or salts can be separated by chromatography over a suitable adsorbent to obtain the individual isomeric reduction products. Chromatographic adsorbents such as silica gel, alumina and the like can be employed to effect the separation. Alternatively, the reduction product mixture can be separated into the respective isomers by fractional recrystallization or by preparative thin layer chromatography according to well known techniques.

The 3-methylenecephalosporins of this invention themselves display relatively low antimicrobial activity. However, they are valuable intermediates in the synthesis desacetoxycephalosporin desacetozycephalosporin antibiotics of high activity.

For example, 3-ethoxythionocarbonylthiomethyl-7(2'-amino-2'-phenylacetamido)-$\Delta^3$-cephem-4-carboxylic acid is hydrogenated in the presence of Raney nickel to provide the reductive displacement product 3-methylene-7-(2'-amino-2'-phenylacetamido)cepham-4-carboxylic acid. The 3-exomethylenecepham reduction product is then isomerized according to the method hereinafter described to provide the desacetoxycephalosporin antibiotic, 3-methyl-7-(2'-amino2'$\lambda$ phenylacetamido)-$\Delta^3$-cephem-4-carboxylic acid (cephalexin).

A further aspect of the present invention, therefore, comprises the conversion of the 3-methylenecephalosporins provided herein, by an isomerization process, to afford 3-methyl-7-acylamido-$\Delta^3$-cephem-4-carboxylic acids. The conversion, as illustrated by the following simplified reaction scheme involves the isomerization of the exo double bond to the endo position, resulting in the formation of the -$\Delta^3$-cephem compound from the 3-methylenecepham compound.

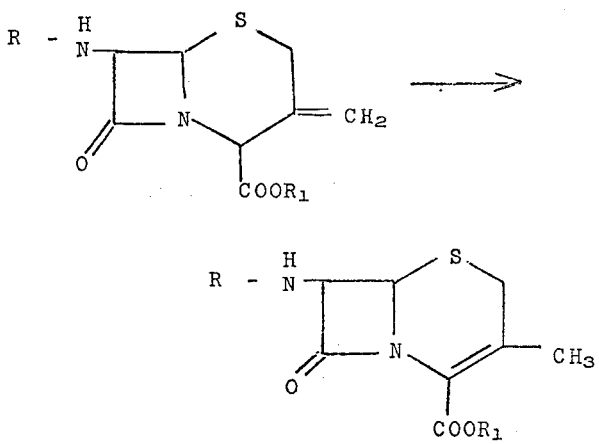

R and $R_1$ have the same meanings as previously defined.

The isomerization is carried out by commingling a 3-methylenecepham acid or ester obtained by the reductive displacement of a 3-substituted methylcephalosporin acid or ester with an aprotic solvent having a dielectric constant and a strongly basic tertiary organic amine. Aprotic solvents which can be employed in the isomerization process are those having a high dielectric constant as for example solvents such as dimethylsulfoxide, dimethylacetamide, dimethylformamide and the like. The preferred solvent of this invention is dimethylacetamide (DMA)

Tertiary organic amines which can be used in the isomerization process in combination with an aprotic solvent include amines having a pK'a of about pK'a 9.5 or greater such as the tertiary alkyl amines containing $C_1$-$C_{10}$ alkyl groups. Illustrative of such amines are trimethylamine, triethylamine, tri-n-propyl amine, methyldiethylamine, tri-n-butylamine, tri-n-octylamine, tri-n-decylamine and the like. The preferred amine of this invention is triethylamine.

The amine is preferably employed in excess of the amount of 3-methylenecepham compound although lesser amounts of amine produce substantial isomerization. In many instances the isomerization proceeds satisfactorily when a few drops or a catalytic amount of the amine is employed.

The isomerization process is conveniently carried out at ambient temperature and appears to proceed at a rapid rate between about 20° and 35°C. However, the isomerization mixture is generally stirred at ambient temperature for about 12 hours to ensure complete isomerization of the exo double bond to the endo position.

The following illustrates the practice of the isomerization process of this invention. One hundred milligrams of 3-methylene-7-[2'-($\alpha$-thienyl)acetamido]-cepham-4-carboxylic acid were dissolved in 5 ml. of dimethylacetamide containing about 15 drops of triethylamine and the reaction mixture was stirred at room temperature for 18 hours. The reaction mixture was poured into a water-ethyl acetate mixture and the mixture acidified to pH 2 with hydrochloric acid. The ethyl acetate layer was separated, was washed with an acid and was then evaporated to dryness to yield 3-methyl-7-[2'-($\alpha$-thienyl)acetamido]-$\Delta^3$-cepham-4-carboxylic acid in 70 percent yield.

The present invention thus provides a method for the preparation of desacetoxycephalosporanic acids or esters from cephalosporanic acids or esters. As previously mentioned, the reduction of a 3-substituted methylcephalosporin of the Formula III in many instances affords an isomeric mixture comprising both a 3-methylenecepham compound and the isomeric $\Delta^3$-cephem compound. In the practice of this invention the isomeric mixture can be separated by known chromatographic or crystallization procedures to provide the individual isomers. The 3-methylenecepham isomer can then be subjected to the isomerization conditions described above to yield the desired $\Delta^3$-cephem antibiotic.

Alternatively, the reduction product mixture comprising the 3-exo and 3-endo isomers can be subjected to the isomerization reaction conditions to provide substantially the desired $\Delta^3$-cephen antibiotic, generally separable by fractional crystallization.

The latter alternative procedure is preferable to the former since it avoids the time-consuming separation methods of chromatography and fractional crystallization at an intermediary stage. In another of its aspects the present invention provides a novel group of compounds represented by the Formula IV.

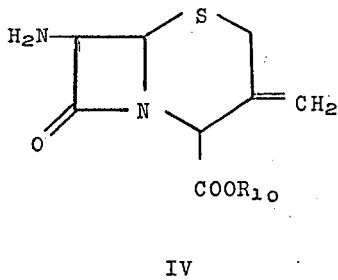

IV wherein $R_{10}$ is hydrogen, $C_1$–$C_4$ alkyl, 4-nitrobenzyl, 4-methoxybenzyl, benzyl, benzyldryl, 2,2,2-trichloroethyl, trimethylsilyl, or a pharmaceutically acceptable cation.

The term "$C_1$–$C_4$ alkyl" refers to methyl, ethyl, n-propyl, isopropyl, n-butyl, sec-butyl, iso-butyl and tert-butyl. The term "pharmaceutically acceptable cation" has the same meaning as previously defined herein.

Illustrative compounds represented by the Formula IV are:
  3-methylene-7-aminocepham-4-carboxylic acid
  3-methylene-7-aminocepham-4-carboxylic acid sodium salt
  3-methylene-7-aminocepham-4-carboxylic acid potassium salt
  3-methylene-7-aminocepham-4-carboxylic acid methyl ester
  3-methylene-7-aminocepham-4-carboxylic acid t-butyl ester
  3-methylene-7-aminocepham-4-carboxylic acid 4-nitrobenzyl ester
  3-methylene-7-aminocepham-4-carboxylic acid trimethylsilyl ester and
  3-methylene-7-aminocepham-4-carboxylic acid 4-methoxybenzyl ester.

The compounds represented by the Formula IV are valuable intermediates in the process for the preparation of desacetoxycephalosporin antibiotics, for example, cephalexin. They are prepared according to the reductive displacement method of this invention, as described above, and undergo isomerization to afford 3-methyl-7-amino-$\Delta^3$-cephem-4-carboxylic acid and esters.

In the practice of the isomerization method of this invention, a 3-methylene-7-aminocepham-4-carboxylic acid or ester thereof is commingled with an aprotic solvent such as dimethylacetamide in the presence of a tertiary amine, preferably thriethyl amine, to effect the isomerization of the exo double bond to the endo position and afford the 3-methyl-7-amino-$\Delta^3$-cephem-4-carboxylic acid or ester (7-ADCA nucleus).

A particularly useful compound of the Formula IV for the preparation of the 7-aminodesacetoxycephalosporanic acid nucleus is the trimethylsilyl ester of 3-methylene-7-aminocepham-4-carboxylic acid ($R_{10}$ = trimethylsilyl). Accordingly, to a suspension of 3-methylene-7-aminocepham-4-carboxylic acid in acetonitrile is added with stirring a trimethylsilylating agent such as N-(trimethylsilyl)acetamide or bis-trimethylsilyl acetamide to form the trimethylsilyl ester. As the ester forms a solution is obtained. Thereafter a tertiary organic amine, such as triethylamine is added to effect the isomerization of the exo double bond to the endo position and provide in solution the trimethylsilyl ester of 7-ADCA. The solution is diluted with water and the pH adjusted to about pH 3.5 to effect the hydrolysis of the trimethylsilyl ester of 7-ADCA with the formation of a crystalline precipitate of 7-ADCA.

The 7-ADCA is filtered and can then be acylated with the desired acyl group, for example, with the amino-protected phenylglycine acyl moiety to provide the antibiotic cephalexin.

Alternatively, the acylation step can be carried out on the trimethylsilyl ester of 7-ADCA prepared in situ and thereafter recovering the trimethylsilyl ester of cephalexin. Hydrolysis of the cephalexin ester with water then provides cephalexin. The acylation of 7-ADCA with an amino-protected phenylglycine, for example, N-(t-butyloxycarbonyl)-protected phenylglycine, can be carried out according to well known acylation procedures. Likewise the hydrolysis of the trimethylsilyl esters of 7-ADCA and cephalexin are carried out by well known procedures.

The following examples more fully illustrate the present invention.

EXAMPLE 1

A solution of one gram of 3-amidinothiomethyl-7-(2'-phenoxyacetamido)-$\Delta^3$-cephem-4-carboxylic acid inner salt in 100 ml. of 50 percent (by volume) aqueous ethanol was hydrogenated at room temperature for 18 hours in an atmosphere of hydrogen gas under 45 psi pressure in the presence of 6 g. of Raney nickel catalyst. the hydrogenation was carried out in a Parr low pressure hydrogenation apparatus. The catalyst was filtered and the filtrate was evaporated in vacuo to remove the ethanol solvent. Ethyl acetate was added to the aqueous concentrate which was then acidified to pH 2.5. The ethyl acetate layer was separated, washed with water, dried over anhydrous magnesium sulfate and evaporated in vacuo to a small volume. On cooling, the ethyl acetate concentrate deposited 3-methylene-7-(2-phenoxyacetamido)-cepham-4-carboxylic acid as a white crystalline compound.

Elemental analysis calculated for $C_{16}H_{16}N_2O_5S$: Theory: C, 55.17; H, 4.63; N, 8.04. Found: C, 55.38; H, 4.86; N, 8.90.

The nuclear magnetic resonance spectrum in dimethylsulfoxide, $d_6$ showed the following signals at the indicated tau values.

6.50 (s, 2H, $C_2H_2$), 5.40 (s, 2H, side-chain $CH_2$), 4.90 (s, 1H, $C_4$ H), 4.72-4.42 (m, 4H, $C_3$, $CH_2$ and $C_6$ H and $C_7$ H and $C_7H$), 3.20-2.60 (m, 5H, aromatic H) and 0.92 (d, 1H, amide NH).

EXAMPLE 2

A solution of one gram of 3-amidinothiomethyl-7-(2-phenylacetamido)-$\Delta^3$-cephem-4-carboxylic acid in 100 ml. of 50 percent (by volume) aqueous ethanol was hydrogenated for 12 hours at room temperature in an atmosphere of hydrogen gas at 45 psi pressure in the presence of 6 g. of Raney nickel catalyst. The catalyst was filtered and the filtrate was evaporated in vacuo to remove ethanol. The aqueous concentrate was slurried with ethyl acetate and the pH was adjusted to pH 2.5 with 1 N hydrochloric acid. The ethyl acetate layer was separated, washed with water and dried over magnesium sulfate. The dried ethyl acetate layer was concentrated to a small volume in vacuo and refrigerated to yield 3-methylene-7-(phenylacetamido)cepham-4-carboxylic acid as white crystals.

Elemental analysis calculated for $C_{16}H_{16}N_2O_4S$: Theory: C, 57.82; H, 4.85; N, 8.43. Found: C, 57.84; H, 5.04; N, 8.31.

EXAMPLE 3

A solution of one gram of 3-amidinothiomethyl-7-[2'-($\alpha$-thienyl)acetamido]-$\Delta^3$-cephem-4-carboxylic acid in 100 ml. of 50 percent (by volume aqueous ethanol was hydrogenated for 12 hours at room temperature in an atmosphere of hydrogen at 45 psi in the presence of 6 g. of Raney nickel catalyst. The catalyst was filtered and washed with water. The filtrate and catalyst wash were combined and evaporated to dryness in vacuo. The residue was dissolved in 25 ml. of water and 50 ml. of ethyl acetate was added. The mixture was acidified to pH 2.5 with 1 N hydrochloric acid and the ethyl acetate layer was separated, dried over magnesium sulfate and evaporated to dryness. The amorphous residue was crystallized from methylene dichloride to yield 3-methylene-7-[2'-($\alpha$-thienyl)acetamido]cepham-4-carboxylic acid as a white crystalline compound.

The nuclear magnetic resonance spectrum in dimethyl sulfoxide, $d_6$ showed the following signals at the indicated tau values: 6.49 (2d, 2H, $C_2$, $H_2$), 6.24 (s, 2H, side-chain $CH_2$), 4.90 (s, 1H, $C_4$ H), 4.72 (s, 2H, $C_3$ $CH_2$), 4.80-4.46 (m, 2H, $C_6$ H and $C_7$ H, overlapping $C_3$ $CH_2$), 3.11-260 (m, 3H, aromatic H) and 0.98 (d, 1H, amide NH).

EXAMPLE 4

One gram of 3-ethoxythionocarbonylthiomethyl-7-[2'-($\alpha$-thienyl)acetamido]-$\Delta^3$-cephem-4-carboxylic acid sodium salt was dissolved in 100 ml. of 50 percent (by volume) aqueous ethanol and the solution was hydrogenated at room temperature overnight in an atmosphere of hydrogen at a pressure of 45 psi. in the presence of 6 g. of Raney nickel catalyst. The catalyst was filtered and the filtrate was concentrated in vacuo by evaporation of ethanol. Ethyl acetate was added to the aqueous concentrate and the pH of the mixture was adjusted to pH 2.5 by the addition of 1 N hydrochloric acid. The ethyl acetate layer was separated, dried and evaporated in vacuo to dryness. The residue was crystallized from methylene chloride to yield 3-methylene-7-[2'-($\alpha$-thienyl)acetamido]-cepham-4-carboxylic acid as a white crystalline compound.

EXAMPLE 5

One gram of 3-benzoylthiomethyl-7-[2'-($\alpha$-thienyl)-acetamido]-$\Delta^3$-cephem-4-carboxylic acid sodium salt was dissolved in 40 ml. of water containing 50 ml. of ethanol and the solution was hydrogenated at room temperature for 12 hours in an atmosphere of hydrogen at a pressure of 45 psi. in the presence of 6 g. of Raney nickel catalyst. The catalyst was filtered and the filtrate was evaporated to dryness in vacuo to yield a mixture of starting material and the reduction product, 3-methylene-7-[2'-($\alpha$-thienyl)-acetamido]cepham-4-carboxylic acid as the sodium salt as determined by thin layer chromatography.

EXAMPLE 6

A solution of 770 mg. of 3-methylmercaptomethyl-7-[2'-($\alpha$-thienyl)acetamido]-$\Delta^3$-cephem-4-carboxylic acid sodium salt was dissolved in 50 ml. of water containing 50 ml. of ethanol and the solution was hydrogenated for 13 hours at room temperature in an atmosphere of hydrogen at a pressure of 45 psi. in the presence of 2.3 g. of Raney nickel catalyst. The catalyst was filtered and the filtrate was evaporated to dryness to yield approximately a 50 percent mixture of the starting material and the reduction product, 3methylene-7-[2'-($\alpha$-thienyl)acetamido]cepham-4-carboxylic acid sodium salt, as determined by thin layer chromatography.

EXAMPLE 7

A solution of one gram of 3-sulfothiomethyl-7-[2'-($\alpha$-thienyl)acetamido]-$\Delta^3$-cephem-4-carboxylic acid disodium salt in 50 percent ethanol was hydrogenated in the presence of 6 g. of Raney nickel under a hydrogen atmosphere maintained at 45 psi. The hydrogenation was conducted for 16 hours at room temperature. The catalyst was filtered and washed with ethanol and the wash was combined with the filtrate and the total was evaporated to dryness in vacuo. A thin layer chromatogram of the solid residual hydrogenation product showed the product to be 3-methylene-7-[2'-($\alpha$-thienyl)-acetamido]cepham-4-carboxylic acid containing a trace of 3-methyl-7-[2'-($\alpha$-thienyl)acetamido]-$\Delta^3$-cephem-4-carboxylic acid.

The solid residue was dissolved in a mixture of ethyl acetate-water and the ethyl acetate layer was separated and was washed with 5 percent hydrochloric acid and with water. The washed ethyl acetate layer was then dried over magnesium sulfate and then was concentrated in vacuo to a volume of about 20 ml. The purified product 3-methylene-7-[2'-($\alpha$-thienyl)acetamido]cepham-4-carboxylic acid crystallized at room temperature and melted at a temperature of about 178°C.

EXAMPLE 8

To a solution of 1.1 g. of benzyl 3-ethoxythionocarbonylthiomethyl-7-[2'-($\alpha$-thienyl)acetamido]-$\Delta^3$-cephem-4carboxylate in 100 ml. of 50 percent aqueous ethanol was added 10 g. of Raney nickel and the mixture was reduced at room temperature in a Parr low pressure hydrogenation apparatus under hydrogen at a pressure of 45 psi. for 18 hours. The catalyst was filtered and the filtrate was evaporated to an aqueous residue. The aqueous residue was extracted with ethyl acetate and the extract was dried over sodium sulfate. The dried extract was evaporated to dryness and the solid residue was recrystallized from a small volume of ethyl acetate to yield a white crystalline product containing 80 percent of benzyl 3-methylene-7-[2'-($\alpha$-thienyl)acetamido]cepham-4carboxylate as shown by the NMR spectrum of the reduction product.

EXAMPLE 9

To a suspension of 1.8 g. of 7-(D-$\alpha$-hydroxy-$\alpha$-phenylacetamido)cephalosporanic acid in 7 ml. of water was added 2 N sodium hydroxide until the pH was adjusted to pH 7. To the resulting neutral solution was added 600 mg. of thiourea and the reaction mixture was heated for 18 hours in a water bath maintained at a temperature of 55°C.

The reaction product crystallized, was filtered, washed with water and was dried in a vacuum desicator to yield 950 mg. of dry crystalline isothiouronium salt, 3-amidinothiomethyl-7-(D-α-hydroxy-α-phenyl)-Δ³-cepham-4-carboxylic acid, inner salt.

Elemental analysis calculated for $C_{17}H_{18}N_4O_5S_2·H_2O$
Calculated: C, 46.35; H, 4.57; N, 12.72. Found: C, 46.54; H, 4.82; N, 12.67.

EXAMPLE 10

A solution of 900 mg. of 3-amidinothiomethyl-7-(D-α-hydroxy-α-phenylacetamido)-Δ³-cepham -4-carboxylic acid inner salt in 50 ml. of water containing 50 ml. of ethanol was hydrogenated for 12 hours at room temperature in an atmosphere of hydrogen at a pressure of 45 psi. in the presence of 6 g. of Raney nickel catalyst. The catalyst was filtered and the filtrate was acidified to pH 2.5. The acidified filtrate was evaporated to remove ethanol and was then extracted with ethyl acetate. The extract was dried and concentrated to a small volume to precipitate the reduction product, 3-methylene-7-(D-α-hydroxy-α-phenylacetamido)-cepham-4-carboxylic acid, as a white crystalline compound.

Elemental analysis calculated for $C_{16}H_{16}N_2O_5S$: Theory: C, 55.16; H, 4.63; N, 8.04. Found: C, 55.29; H, 4.91; N, 7.75.

Thin layer chromatography of a sample of the crystalline reduction product indicated the presence of two minor impurities.

EXAMPLE 11

Two grams of 3-[5-(1-methyltetrazolyl)thiomethyl]-7-[2'-(αthienyl)acetamido]-Δ³-cephem-4carboxylic acid sodium salt were dissolved in 100 ml. of 50 percent aqueous ethanol and 10 g. of Raney nickel were added to the solution. The mixture was reduced under 40 psi. of hydrogen pressure at room temperature for 18 hours. The catalyst was filtered and the filtrate was evaporated to remove ethanol. The aqueous residue was acidified with dilute hydrochloric acid and then extracted with ethyl acetate. The extract was washed with water and dried. Evaporation of the dried extract yielded a mixture comprising 3-methylene-7-[2-(α-thienyl)acetamido]cepham-4-carboxylic acid and 3-methyl-7-[2-(α-thienyl)acetamido]-Δ³-cephem-4-carboxylic acid as determined by a thin layer chromatographic comparison with authentic samples of each compound.

The product mixture was fractionally recrystallized from methylene chloride to yield 500 mg. of the 3-methylene product was a white crystalline compound.

EXAMPLE 12

Two grams of 3-[5(1-methyltetrazolyl)thiomethyl]-7-[2'- (α-thienyl)acetamido]Δ³ -cephem-4-carboxylic acid sodium salt was dissolved in 16 ml. of tetrahydrofuran containing 5 ml. each of water, dimethylformamide and formic acid, and 2.8 grams of zinc dust was added to the solution. The reduction mixture was stirred at room temperature for 18 hours and filtered. The filtrate was evaporated to remove tetrahydrofuran and the aqueous acidic residue was extracted with ethyl acetate. The extract was washed with 5 percent aqueous hydrochloric acid and with water and was then dried. The dry extract was evaporated to a small volume and on dilution with ether deposited a crystalline mixture of the reduction products, 3-methylene-7-[2-(α-thienyl)acetamido]cepham-4-carboxylic acid and 3-methyl-7-[2'-(α-thienyl)acetamido]-Δ³-cephem-4-carboxylic acid.

The crystalline mixture was fractionally recrystallized from methylene chloride to yield 700 mg. of 3-methylene-7-[2-(α-thienyl)acetamido]cepham-4-carboxylic acid as a white crystalline solid.

EXAMPLE 13

To a solution of 300 mg. of 3-ethoxythionocarbonyl-thiomethyl-7-phenoxyacetamido-Δ³-cephem-4-carboxylic acid sodium salt in 5.5 ml. of tetrahydrofuran, 1.5 ml. water, 1.5 ml. of formic acid and 1.5 ml. of DMF was added 700 mg. of zinc dust and the reduction mixture was stirred at room temperature for about 18 hours. The zinc was filtered and the filtrate was concentrated in vacuo. The concentrate was taken up in ethyl acetate-water, acidified to pH 2.5 and the ethyl acetate layer was separated and washed successively with 5 percent hydrochloric acid and water and dried. The dried ethyl acetate layer was evaporated to dryness. The NMR spectrum of the residue showed the residue was comprised mainly of 3-methylene-7-phenoxyacetamidocepham4-carboxylic acid and some unreacted starting material.

EXAMPLE 14

A solution of 500 mg. of 3-benzoylthiomethyl-7-[2'-(α-thienyl)acetamido]-Δ³-cephem-4-carboxylic acid sodium salt was dissolved in a solvent mixture containing 5.5 ml. of tetrahydrofuran, 1.5 ml. of water, 1.5 ml. of formic acid and 1.5 ml. of dimethylformamide. Five grams of zinc dust were added and the reaction mixture was stirred and heated at 50°C. for 6 hours. The reaction mixture was allowed to cool to room temperature, and filtered and the filtrate was evaporated in vacuo to remove the tetrahydrofuran. The residue was dissolved in a mixture of ethyl acetate and water, acidified to pH 2.5 and the ethyl acetate layer was separated. The ethyl acetate layer was washed with 5 percent hydrochloric acid and water and was then dried. The ethyl acetate was evaporated to a small volume and diluted with 3 volumes of ether to precipitate the reduction product, 3-methylene-7-[2'-(α-thienyl)acetamido]cepham-4-carboxylic acid, as a white crystalline solid.

EXAMPLE 15

To a solution of 8.2 g. of 3 amidinothiomethyl-7-[2'-(α-thienyl)acetamido]-Δ³-cephem-4-carboxylic acid inner salt in a solvent mixture comprising 60 ml. of tetrahydrofuran, 20 ml. of DMF, 20 ml. of formic acid and 25 ml. of water was added 13 g. of zinc dust and the mixture was stirred at room temperature overnight. The zinc was filtered from the reaction mixture and washed with tetrahydrofuran. The filtrate and wash were combined and concentrated in vacuo to remove the low boiling solvent. The residue was dissolved in a mixture of water and ethyl acetate and the organic layer separated. The separated layer was washed with 5 percent hydrochloric acid and with water and then dried. The dried solution was evaporated to a small volune in vacuo to obtain 4 g. of 3 -methylene-7-[2'-(α-thienyl)acetamido]cepham-4-carboxylic acid.

EXAMPLE 16

Five grams of 3-benzoylthiomethyl-7-[2'-(α-thienyl)-acetamido]-Δ³-cephem-4-carboxylic acid sodium salt was dissolved in a mixture of 55 ml. of tetrahydrofuran, 15 ml. of DMF, 15 ml. of formic acid and 15 ml. of water. To the solution was added 7 g. of zinc dust and the mixture was stirred at room temperature for 12 hours. The reaction mixture was filtered and the zinc washed on the filter with tetrahydrofuran. The filtrate and zinc wash were combined and concentrated in vacuo to remove the more volatile solvents. The concentrate was taken up in ethyl acetate water and the ethyl acetate layer separated. The ethyl acetate solution was washed with 5 percent hydrochloric acid and water before drying over magnesium sulfate. The dried solution was then concentrated in vacuo to a volume of 20 ml. to precipitate 1.2 g. of the reaction product, 3-methylene-7-[2'-($\alpha$-thienyl)acetamido]-cepham-4-carboxylic acid, melting at about 178°C. The following physical data obtained on the above product is in agreement with its designated structure:

NMR spectrum: (in $CDCl_3$-DMSO $d_6$) in tau values: 6.52 (2d, 2H, $C_2$ $H_2$), 6.20 (s, 2H, side-chain $CH_2$), 4.98 (s, 1H, $C_4$ H), 4.77 (s, 2H, $C_3$ $CH_2$), 4.70-4.32 (m, 2H, $C_6$ H and $C_7$ H), 3.10-2.8 (m, 3H, aromatic H) and 1.72 (d, 1H, amide NH).

Infrared Absorption Spectrum: (Nujol mull) in microns 2.95 (amide NH), 5.7 ($\beta$-lactam carbonyl), 5.75 (carboxyl carbonyl), 6.1 and 6.6 (amide carbonyl).

Electrometric titration in 66 percent aqueous DMF shows the presence of one titratable group having a pKa value of 4.4.

The molecular weight based on the above titration data was 335(calculated, 338).

Elemental analysis calculated for $C_{14}H_{14}N_2O_4S$: Theory: C, 49.71; H, 4.17; N, 8.28. Found: C, 49.58; H, 4.36; N, 8.25.

The filtrate obtained after filtering off the reaction product from the ethyl acetate concentrate was shown by NMR and thin layer chromatography to contain additional amounts of 3-methylene-7-[2'-($\alpha$-thienyl)acetamido]cepham-4-carboxylic acid and the isomeric 3-methyl-7-[2'-($\alpha$-thienyl)acetamido]-$\Delta^3$-cephem4-carboxylic acid.

EXAMPLE 17

To a solution of 500 mg. of 3-benzoylthiomethyl-7-[2'-($\alpha$-thienyl)acetamido]-$\Delta^3$-cephem-4-carboxylic acid sodium salt in a solvent mixture comprising 5.5 ml. of tetrahydrofuran, 1.5 ml. of water, 1.5 ml. of formic acid and 2 drops of DMF was added one gram of zinc dust and the mixture was stirred at room temperature for 24 hours. The reaction mixture was filtered and the filtrate concentrated in vacuo. The residue was diluted with water and extracted with ethyl acetate. The extract was washed with 5 percent hydrochloric acid and with water and dried. The dried extract was evaporated to dryness to obtain the reduction product as an amorphous residue. The residue was slurried with methylene chloride to provide 222 mg. of crystalline product 3-methylene-7-[2'-($\alpha$-thienyl)acetamido]cepham-4-carboxylic acid.

EXAMPLE 18

One gram of 3amidinothiomethyl-7-[2'-($\alpha$-thienyl)-acetamido]-$\Delta^3$-cephem-4-carboxylic acid was dissolved in a solvent mixture comprising 5.5 ml. of tetrahydrofuran, 1.5 ml. of water, 1.5 ml. of DMF and 1.5 ml. of formic acid. The reaction solution was cooled to a temperature of 0°–5°C. and was stirred for 24 hours with 1.4 g. of zinc dust. The reation mixture was filtered and the filtrate concentrated in vacuo. Water was added to the concentrate which was then extracted with ethyl acetate. The extract was washed with 5 percent hydrochloric acid and with water and dried. The dried extract was evaporated in vacuo to obtain a mixture of 3-methylene-7-[2'-$\alpha$-thienyl)acetamido]-cephem-4-carboxylic acid and 3-methyl-7-[2'-($\alpha$-thienyl)acetamido]-$\Delta^3$-cephem-4-carboxylic acid in a ratio of about 4:1 respectively.

EXAMPLE 19

A solution of 11 g. (31 mmole) of 3-ethoxythionocarbonylthiomethyl-7-amino-$\Delta^3$-cephem-4-carboxylic acid sodium salt in 260 ml. of a 5 percent solution of sodium bicarbonate containing 40 ml. of ethanol was hyrogenated for 12 hours under a hydrogen pressure of 45 psi. at room temperature in the presence of 66g. of Raney nickel catalyst. The reaction mixture was filtered to remove the catalyst and the filtrate was cooled in an ice bath and acidified to pH 3.5 with concentrated hydrochloric acid. A precipitate of unreacted starting material (ca. 2.2g.) was filtered and the filtrate was evaporated in vacuo to a small volume. The crude reaction product precipitated from the concentrate and was filtered. The crude reaction product was crystalized from water to give 4.5g. (85% yield) of pure 3-methylene-7-aminocepham-4-carboxylic acid.

The nuclear magnetic resonance spectrum of the product in DMSO $d_6$ gave the following signals at the indicated tau values: 6.49 (g, 2H, $C_2$ $H_2$), 5.46 (d, 1H, $C_6$H), 5.07 (s, 1H, $C_4$H), 4.80 (broad s, 3H, $C_3$ $CH_2$ and $C_7$H) and 4.13 (broad s, washed out by $D_2O$).

The mass spectrum gave a peak at 214 m/e corresponding to $C_8H_{10}N_2O_3S$, with the calculated molecular weight of 214.2.

The infrared spectrum showed bands at 5.65 ($\beta$-lactam) and 6.1 (carboxylate) microns.

Elemental analysis calculated for $C_8H_{10}N_2O_3S$: Theory: C, 44.85; H, 4.70; N, 13.08. Found: C, 45.12; H, 4.73; N, 13.11.

EXAMPLE 20

Five grams of 3-benzoylthiomethyl-7-($\alpha$-thienyl)-acetamido-$\Delta^3$-cephem-4-carboxylic acid sodium salt was nearly all dissolved in 50 ml. of dimethylacetamide and 2.9 g. of benzyl bromide was added to the solution with stirring. The mixture was stirred overnight at room temperature and was then taken up in a large volume of water-ethyl acetate mixture. The ethyl acetate layer was separated and was washed with 5 percent hydrochloric acid and with water. The washed ethyl acetate solution was then dried and evaporated in vacuo to a smaller volume. On cooling, 4.5 g. of benzyl 3-benzoylthiomethyl-7-[2'-($\alpha$-thienyl)acetamido]-$\Delta^3$-cephem-4-carboxylate slowly crystallized. Melting point 150°–151°C.

Elemental analysis calculated for $C_{28}H_{24}N_2O_5S_3$ Calculated: C, 59.56; H, 4.28; N, 4.96. Found: C, 59.53; H, 4.57; N, 5.12.

EXAMPLE 21

To a solution of one gram of benzyl 3-benzoylthiomethyl-7-[2'-($\alpha$-thienyl)acetamido]-$\Delta^3$-cephem-4-carboxylate in a solvent mixture of 6 ml. of tetrahydrofuran, 1.5 ml. of DMF, 1.5 ml. of water and 1.5 ml. of formic acid was added 1.4 g. of zinc dust and the reduction mixture was stirred at room temperature for 18 hours. The zinc was filtered and the filtrate was concentrated by evaporation in vacuo. The concentrate was taken up in waterethyl acetate and the ethyl acetate layer was separated and washed with 5 percent hydrochloric acid and water before being dried over magnesium sulfate. The dried ethyl acetate solution was evaporated to dryness and the residue was crystallized from benzene-ether to yield 800 mg. of a crystalline product comprising a 3:2 mixture of benzyl 3-methyl-7-[2'-($\alpha$-thienyl)acetamido]-$\Delta^3$-cephem-4-carboxylate and benzyl 3-methylene -7-[2'-($\alpha$-thienyl)acetamido]-cepham-4-carboxylate respectively as shown by the NMR spectrum of the product mixture.

The NMR (CDCl$_3$) showed signals at the following tau values:

7.86 (s, C$_3$ methyl)
6.68 (2d, 2H, C$_2$ hydrogen)
6.15 (s, 2H, side-chain methylene)
5.03 (d, 1H, C$_6$ - hydrogen)
4.82-4.57 (m, C$_4$-hydrogen, C$_3$-methylene and ester CH$_2$)
4.21 g, 1H, C$_7$-hydrogen)
3.15-2.56 (m, aromatic hydrogen)

EXAMPLE 22

A solution of 570 mg. of 3-benzoylthiomethyl-7-[2'-($\alpha$-thienyl)acetamido]-$\Delta^3$-cephem-4-carboxylic acid sodium salt in 10 ml. of tetrahydrofuran, 10 ml. of water and 10 ml. of DMF was added to chromous chloride (prepared from 5 g. of chromium chloride in an atmosphere of carbon dioxide) and the reaction mixture was stirred at room temperature for 3 hours. The reaction mixture was evaporated and the residue was taken up in ethyl acetate. The ethyl acetate was then washed with water and dried. Evaporation of the dried ethyl acetate product solution yielded a reaction product mixture comprising mainly 3-methylene-7-[2-($\alpha$-thienyl) acetamido] cepham-4-carboxylic acid. Thin layer chromatography showed the presence of starting material as well as a minor amount of 3-methyl-7-[2-($\alpha$-thienyl) acetamido]-$\Delta^3$-cephem-4- carboxylic acid.

EXAMPLE 23

To a solution of two grams of 3-amidinothiomethyl-7-[2'-($\alpha$-thienyl) acetamido]-$\Delta^3$-cephem-4-carboxylic acid in 8 ml. of DMF and 3 ml. of ethanol was added one gram of finely cut aluminum foil and 60 mg. of mercuric chloride. The reaction mixture was stirred in a water bath maintained at a temperature of 50°C. for 1.5 hours. The reaction mixture was cooled to room temperature and poured into a water-ethyl acetate mixture. The organic layer was separated and was washed successively with 5 percent hydrochloric acid and water and then dried. The dried organic layer was evaporated to dryness to yield 100 mg. of a crystalline mixture comprising mainly 3-methylene-7-[2-($\alpha$-thienyl) acetamido]-cepham-4-carboxylic acid as shown by its NMR Spectrum.

EXAMPLE 24

To a solution of 700 mg. of 3-methylene-7-[2'-($\alpha$-thienyl)-acetamido]cepham-4-carboxylic acid sodium salt in 7 ml. of dimethylacetamide was added 600 mg. of anisyl bromide and the mixture was stirred at room temperature overnight. The precipitate was filtered and crystallized from ethyl acetate to yield p-methoxybenzyl 3-methylene-7-[2'-($\alpha$-thienyl) acetamido] cepham-4-carboxylate melting at about 114°C.

Elemental analysis calculated for $C_{22}H_{22}N_2O_5S_2$: Calculated: C, 57.64; H, 4.84; N, 6.11. Found: C, 57.76; H, 4.94; N, 6.02.

NMR spectrum (in CDCl$_3$) showed signals at the following tau values:

6.65 (2d, 2H, C$_2$-H)
4.20 (s, 5H, ester -OCH$_3$, and side chain CH$_2$)
4.90 - 4.8 (m, 5H, C$_4$-H, C$_3$ methylene and ester CH$_2$)
4.66 (d, 1H, C$_6$-H)
4.27 (g, 1H, C$_7$-H) and
3.3 - 2.66 (m, 8-H, amide N-H and aromatic hydrogen)

EXAMPLE 25

A suspension of 677 mg. of 3-methylene-7-[2'-($\alpha$-thienyl)-acetamido] cepham-4-carboxylic acid in 30 ml. of water was converted to the sodium salt by adjusting the pH of the suspension to pH 5.5 with 1 N sodium hydroxide. The salt solution was filtered and evaporated to dryness in vacuo to obtain the dry solid sodium salt.

The sodium salt was dissolved in 20 ml. of DMA and 475 mg. of p-nitrobenzyl bromide were added with stirring. The reaction mixture was stirred at room temperature for about 18 hours and was then evaporated in vacuo. The residue was dissolved in ethyl acetate and the solution was washed sucessively with 5 percent sodium bicarbonate and water. The solution was then dried and evaporated to a small volume. The reaction product crystallized to yield 300 mg. of p-nitrobenzyl 3-methylene-7-[2'-($\alpha$-thienyl)-acetamido]cepham-4-carboxylate melting at about 157° C.

The nuclear magnetic resonance spectrum of the product showed the following signals at the indicated tau values:

6.46 (2d, 2H, C$_2$ H$_2$)
6.21 (s, 2H, side-chain CH$_2$)
4.71 (s, 1H, C$_4$H)
4.63 (s, 2H, C$_3$ CH$_2$)
4.55 (s, 2H, ester CH$_2$)
4.7-4.39 (m, 2H, C$_6$H and C$_7$H)
3.1-1.6 (m. 7H, aromatic H)
0.82 (d, 1H, amide NH)

The infrared spectrum (nujol mull) showed the following absorption maxima at the indicated wavelength in microns:

5.70 ($\beta$-lactam carbonyl)
5.75 (ester carbonyl)
6.0 and 6.5 (amide carbonyl)

The ultraviolet absorption spectrum (in ethanol) showed absorption bands at 237 $\mu$ (E = 10,700) and 264 $\mu$ (e = 9,000).

Elemental analysis calculated for $C_{21}H_{19}N_3O_6S_2$: Theory: C, 53.28; H, 4.05; N, 8.88. Found: C, 53.09; H, 4.32; N, 8.61.

EXAMPLE 26

To 5 ml. of dimethylacetamide containing 4 drops of triethylamine was added 100 mg. of p-nitrobenzyl 3-methylene-7-[2'-($\alpha$-thienyl) acetamido] cepham-4-carboxylate and the solution obtained thereby was stored at room temperature overnight. The reaction mixture was poured into a mixture of water-ethyl acetate and the ethyl acetate layer was separated and washed with 5 percent hydrochloric acid and water before drying over magnesium sulfate. The dried ethyl acetate layer was evaporated to dryness to yield p- nitrobenzyl 3-methyl-7-[2'-(α-thienyl) acetamido]-Δ³-cephem-4-carboxylate as a white crystalline solid.

EXAMPLE 27

To 5 ml. of dimethylacetamide containing 15 drops of triethylamine was added 100 mg. of 3-methylene-7-[2'-(Δ-thienyl)-acetamido]cepham-4-carboxylic acid and the solution was stored at room temperature overnight. The reaction mixture was poured into a mixture of water-ethyl acetate and immediately acidified to pH 2 with 5 percent hydrochloric acid. The ethyl acetate layer was separated and was washed with 5 percent hydrochloric acid and water and was then dried over magnesium sulfate. The dried ethyl acetate layer was evaporated to dryness in vacuo to yield a solid residual product which on examination of its NMR spectrum and its silica gel thin layer chromatogram was shown to comprise 70 percent of the isomerized product, 3-methyl-7-[2'-(α-thienyl)-acetamido]-Δ³-cephem-4-carboxylic acid.

EXAMPLE 28

To a well stirred suspension of one gram of 3-methylene-7-aminocepham-4-carboxylic acid in 20 ml. of acetonitrile was added 3 g. of N-(trimethylsilyl) acetamide. To the resulting solution 3 drops of triethylamine were added and the reaction solution was stirred at room temperature for 2 hours. The reaction solution was diluted with water and the pH of the solution adjusted to pH 3.5 with hydrochloric acid. The reaction product, 3-methyl-7-amino-Δ³-cephem-4-carboxylic acid (7-ADCA) formed as a crystalline precipitate from the acidified reaction solution.

I claim:
1. The process for preparing a compound of the formula

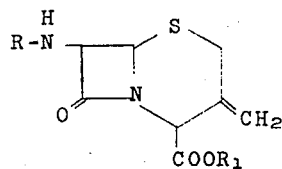

which comprises reducing a 3-substituted methyl-Δ³-cephem compound of the formula

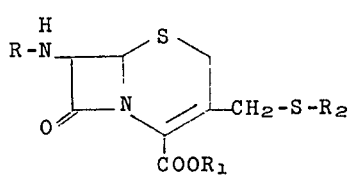

in an inert solvent (1) in the presence of hydrogen and a nickel or cobalt hydrogenation catalyst at a temperature between 25° and 45°C. or (2) in the presence of dimethylformamide at a temperature between 0° and 60°C. with a reducing agent selected from the group consisting of
 a. aluminum amalgam,
 b. zinc in the presence of an acid,
 c. zinc amalgam in the presence of an acid,
 d. zinc-copper couple in the presence of an acid, and
 e. chromium II cations in the presence of an acid, wherein b-e, said acid is a carboxylic acid having a pK'a of pK'a 4.0 or lower or a dilute mineral acid at a concentration between 0.5 and 5 percent;

wherein in the foregoing formulae
 $R_1$ is hydrogen, $C_1$–$C_4$ alkyl, benzyl, p-methoxybenzyl, benzhydryl, 4-methoxybenzhydryl and phenacyl; or a pharmaceutically acceptable cation;
 R is hydrogen, $C_1$–$C_8$ alkanoyl, $C_6$–$C_{10}$ cycloalkanoyl, $C_2$–$C_8$ hydroxyalkanoyl, $C_3$–$C_8$ alkanoyl substituted by carboxy and amino or protected amino, benzoyl, $C_1$–$C_3$ alkylbenzoyl, $C_1$–$C_3$ alkoxybenzoyl, halobenzoyl, aminobenzoyl, or an acyl group represented by the formula

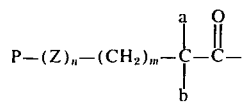

wherein
 P is α-thienyl, β-thienyl, α-furyl, β-furyl, benzothienyl, benzofuryl, phenyl, $C_1$–$C_3$ alkylphenyl, $C_1$–$C_3$ alkoxyphenyl, hydroxyphenyl, halophenyl or aminophenyl,
 Z is oxygen or sulfur,
 n is 0 or 1,
 m is an integer of from 0 to 3,
 a is hydrogen or $C_1$–$C_3$ alkyl,
 b is hydrogen, $C_1$–$C_3$ alkyl, hydroxy, or amino,
with the limitation that when
 n is 1, P is phenyl, $C_1$–$C_3$ alkylphenyl, $C_1$–$C_3$ alkoxyphenyl, hydroxyphenyl, halophenyl or aminophenyl and b is hydrogen or $C_1$–$C_3$ alkyl.
 $R_2$ is $C_2$–$C_4$ alkanoyl, $C_2$–$C_4$ haloalkanoyl, benzoyl, $C_1$–$C_3$ alkylbenzoyl, $C_1$–$C_3$ alkoxybenzoyl, halobenzoyl, or aminobenzoyl, $C_1$–$C_4$ alkyl, $C_1$–$C_{12}$ alkoxythionocarbonyl, an amidino group of the formula

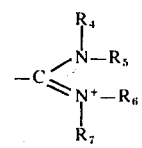

wherein
 $R_4$, $R_5$, $R_6$ and $R_7$ are the same or different, and represent hydrogen, $C_1$–$C_6$ alkyl, $C_3$–$C_7$ cycloalkyl, phenyl, phenyl substituted by $C_1$–$C_4$ lower alkyl, halogen, amino or hydroxy, naphthyl, benzyl, 2-phenethyl, 3-phenylpropyl, naphthylmethyl or 2-naphthylethyl,
a thiocarbamoyl group of the formula

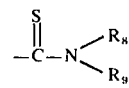

wherein
 $R_8$ and $R_9$ when taken separately are the same or different and are hydrogen, $C_1$–$C_6$ alkyl, phenyl, $C_1$–$C_3$ alkylphenyl, $C_1$–$C_3$ alkoxyphenyl, halophenyl, hydroxyphenyl or aminophenyl, and $R_8$ and $R_9$ when taken together form a 4 or 5 membered alkylene, azaalkylene or oxaalkylene bridge;
a heteroaryl group selected from the group consisting of pyridyl, 2-pyrimidyl, 2-imidazolyl, 2-thiazolyl, 2-benzthiazolyl, 2-benzoxazolyl, 2-tetrazolyl, 1-methyl-2-tetrazolyl, thiadiazolyl and 2-methyl-5-thiadiazolyl; or a group of the formula -SO$_3$-M$^+$ wherein M$^+$ is an alkali or alkaline earth metal cation; such that when R$_2$ is amidino or substituted amidino group, R$_1$ is hydrogen or when R$_2$ is —SO$_3$—M$^+$, R$_1$ is M$^+$.

2. The process of claim 1 wherein the reduction is carried out in the presence of hydrogen and a nickel or cobalt hydrogenation catalyst.

3. The process of claim 2 wherein the hydrogenation catalyst is Raney nickel.

4. The process of claim 1 wherein the reduction is carried out in the presence of dimethylformamide with a reducing agent selected from the group consisting of aluminum amalgam, zinc, zinc amalgam, zinc-copper couple and chromium II cations.

5. The process of claim 4 wherein the reducing agent is zinc in the presence of formic acid.

6. The process of claim 4 wherein the reducing agent is zinc in the presence of hydrochloric acid at a concentration between 0.5 and 5 percent.

7. The process of claim 3 wherein the compound reduced is 3-amidinothiomethyl-7-(2'-phenoxyacetamido)-Δ$^3$-cephem-4-carboxylic acid inner salt.

8. The process of claim 3 wherein the compound reduced is 3-ethoxythionocarbonylthiomethyl-7-[2'-(α-thienyl)-acetamido]-Δ$^3$-cephem-4-carboxylic acid.

9. The process of claim 3 wherein the compound reduced is 3-methylmercaptomethyl-7-[2'-(α-thienyl)acetamido]-Δ$^3$-cephem-4-carboxylic acid sodium salt.

10. The process of claim 3 wherein the compound reduced is 3-ethoxythionocarbonylthiomethyl-7-amino-Δ$^3$-cephem-4-carboxylic acid.

11. The process of claim 3 wherein the compound reduced is 3-ethoxythionocarbonylthiomethyl-7-(5'-propionamido-5'-carboxyvaleramido)-Δ$^3$-cephem-4-carboxylic acid.

12. The process of claim 3 wherein the compound reduced is 3-ethoxythionocarbonylthiomethyl-7-(5'-acetamido-5'-carboxyvaleramido)-Δ$^3$-cephem-4-carboxylic acid.

13. The process of claim 4 wherein the compound reduced is 3-benzoylthiomethyl-7-(2'-amino-2'-phenylacetamido)-Δ$^3$-cephem-4-carboxylic acid.

14. The process of claim 2 wherein the compound reduced is disodium 3-sulfothiomethyl-7-[2'-(α-thienyl) acetamido]-Δ$^3$-cephem-4-carboxylate.

15. The process for converting a 3-methylenecepham compound of the formula

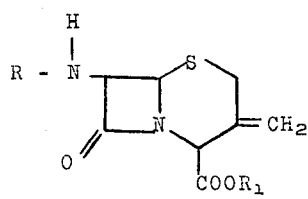

to a Δ$^3$-cephem compound of the formula

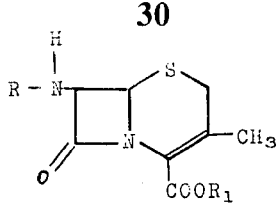

which comprises commingling said 3-methylenecepham with an aprotic solvent having a high dielectric constant and a tertiary amine having a pK'a of at least pK'a 9.5 wherein the foregoing formulae R$_1$ is hydrogen, a carboxylic acid protecting group, or a pharmaceutically acceptable cation;

R is hydrogen, C$_1$-C$_8$ alkanoyl, C$_6$-C$_{10}$ cycloalkanoyl, C$_2$-C$_8$ hydroxyalkanoyl, C$_3$-C$_8$ alkanoyl substituted by carboxy and amino or protected amino, benzoyl, C$_1$-C$_3$ alkylbenzoyl, C$_1$-C$_3$ alkoxybenzoyl, halobenzoyl, aminobenzoyl, or an acyl group represented by the formula

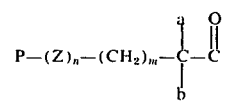

wherein

P is α-thienyl, β-thienyl, α-furyl, β-furyl, benzothienyl, benzofuryl, phenyl, C$_1$-C$_3$ alkylphenyl, C$_1$-C$_3$ alkoxyphenyl, hydroxyphenyl, halophenyl or aminophenyl, Z is oxygen or sulfur, n is 0 or 1, m is an integer of from 0 to 3, a is hydrogen or C$_1$-C$_3$ alkyl, b is hydrogen, C$_1$-C$_3$ alkyl, hydroxy, amino or or protected amino, with the limitation that when n is 1, P is phenyl C$_1$-C$_3$ alkylphenyl, C$_2$-C$_3$ alkoxyphenyl, hydroxyphenyl, halophenyl or aminophenyl and b is hydrogen or C$_1$-C$_3$ alkyl.

16. The process of claim 14 wherein the aprotic solvent is dimethylacetamide and the tertiary amine is triethylamine.

17. A compound of the formula

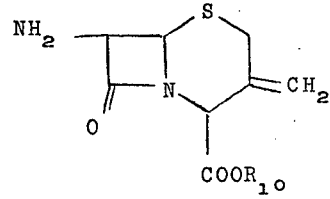

wherein R$_{10}$ is hydrogen, C$_1$-C$_4$ alkyl, 4-nitrobenzyl, 4-methoxybenzyl, 2,2,2-trichloroethyl, trimethylsilyl, or a pharmaceutically acceptable cation.

18. A compound of the formula

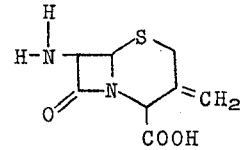

19. The process of claim 4 wherein the compound reduced is 3-benzoylthiomethyl-7-[2'-(α-thienyl)acetamido]-Δ$^3$-cephem-4-carboxylic acid.

* * * * *